US011645552B2

(12) United States Patent
Bastide et al.

(10) Patent No.: US 11,645,552 B2
(45) Date of Patent: May 9, 2023

(54) TRAVEL HEALTH OPTIMIZATION SIMULATING HEALTH IMPACT OF INTENDED USER TRAVEL USING COGNITIVE ANALYTICS BASED ON CONDITIONS AT A GEOGRAPHIC LOCATION

(71) Applicant: International Business Machines Corporation, Armonk, NY (US)

(72) Inventors: Paul R. Bastide, Boxford, MA (US); Sunil K. Mishra, Morrisville, NC (US); Anca Sailer, Scarsdale, NY (US); Mattia Tomasoni, Dublin (IE); Benjamin Wisnewski, Columbia, MO (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 988 days.

(21) Appl. No.: 15/917,754

(22) Filed: Mar. 11, 2018

(65) Prior Publication Data

US 2019/0279069 A1 Sep. 12, 2019

(51) Int. Cl.
G06N 5/04 (2023.01)
G06N 20/00 (2019.01)
G16H 50/30 (2018.01)

(52) U.S. Cl.
CPC ............ *G06N 5/04* (2013.01); *G06N 20/00* (2019.01); *G16H 50/30* (2018.01)

(58) Field of Classification Search
CPC .......................... G06N 3/006; G06N 5/04
See application file for complete search history.

(56) References Cited

U.S. PATENT DOCUMENTS 6,558,164 B2    5/2003  Raha
7,523,044 B2 *  4/2009  Rosenblood ........... G16H 10/60
                                             348/211.3

(Continued)

FOREIGN PATENT DOCUMENTS

CN         112998650 A  *  6/2021  ........... A61B 5/0002
WO   WO-2018025008 A1  *  2/2018  ............. A61B 5/725

OTHER PUBLICATIONS

Disclosed Anonymously, Resolve User Medical Symptom Based on Real Time Location, Oct. 19, 2016, IP.com, URL: https://priorart.ip.com/IPCQM/000248034 (Year: 2016).*

(Continued)

*Primary Examiner* — Lut Wong
(74) *Attorney, Agent, or Firm* — Cuenot, Forsythe & Kim, LLC

(57) ABSTRACT

A geographic location to which a user intends to travel, medical information pertaining to the user and conditions at the geographic location that impact health of human beings can be identified. A health impact model can be created for the user, the health impact model analyzing the determined conditions at the geographic location in a context of the accessed medical information pertaining to the user. Based on the analyzing by the health impact model, a score can be assigned to an anticipated health impact on the user of the identified conditions at the geographic location. If the score assigned to the anticipated health impact on the user of the identified conditions at the geographic location exceeds a threshold value, at least one action for the user can be automatically initiated and controlled.

20 Claims, 3 Drawing Sheets

(56) References Cited

U.S. PATENT DOCUMENTS

| | | | | |
|---|---|---|---|---|
| 7,558,738 | B1* | 7/2009 | Flatt | G06Q 30/02 705/2 |
| 8,930,226 | B1* | 1/2015 | Kerr | G16H 15/00 705/3 |
| 9,009,167 | B2* | 4/2015 | Cerny | G06F 16/9535 707/749 |
| 10,366,791 | B1* | 7/2019 | Thiagarajan | G16H 50/80 |
| 10,388,406 | B2* | 8/2019 | Riley | G16H 10/20 |
| 2002/0147135 | A1 | 10/2002 | Schnell | |
| 2002/0184055 | A1* | 12/2002 | Naghavi | G16H 40/63 705/2 |
| 2003/0130708 | A1* | 7/2003 | Von Arx | A61N 1/37282 607/60 |
| 2004/0172284 | A1* | 9/2004 | Sullivan | G16H 40/67 705/2 |
| 2005/0234748 | A1* | 10/2005 | Kaplan | G06Q 10/02 705/5 |
| 2006/0100908 | A1 | 5/2006 | Becker et al. | |
| 2007/0214013 | A1* | 9/2007 | Silverman | G16H 20/40 600/300 |
| 2008/0033751 | A1* | 2/2008 | Greene | G16H 20/30 705/2 |
| 2008/0215627 | A1* | 9/2008 | Higgins | G16H 10/60 |
| 2008/0306768 | A1* | 12/2008 | Fotsch | G06Q 10/10 705/2 |
| 2009/0015413 | A1* | 1/2009 | Gelabert | G06K 19/0716 340/572.1 |
| 2009/0138287 | A1* | 5/2009 | Hermann, Jr. | G16H 40/20 707/999.009 |
| 2009/0210262 | A1* | 8/2009 | Rines | G06Q 10/06 705/5 |
| 2011/0178812 | A1* | 7/2011 | Lindsay | G16H 20/10 705/2 |
| 2011/0258002 | A1* | 10/2011 | Green, III | G16H 10/60 705/3 |
| 2012/0130742 | A1* | 5/2012 | Church | G16H 40/67 705/3 |
| 2012/0157795 | A1 | 6/2012 | Chiu et al. | |
| 2012/0158422 | A1* | 6/2012 | Burnham | G06Q 10/00 705/2 |
| 2013/0166607 | A1* | 6/2013 | Turk | G06Q 50/14 707/E17.032 |
| 2014/0167917 | A2* | 6/2014 | Wallace | G16H 40/67 340/10.1 |
| 2015/0100330 | A1* | 4/2015 | Shpits | G16H 50/80 705/2 |
| 2015/0363694 | A1* | 12/2015 | Banerjee | G06N 5/02 706/46 |
| 2016/0063215 | A1* | 3/2016 | Zamer | G16H 40/63 705/3 |
| 2016/0125152 | A1* | 5/2016 | Higgs | G16H 10/60 705/3 |
| 2016/0140830 | A1* | 5/2016 | Hathorn | G08B 21/18 340/686.6 |
| 2016/0232321 | A1* | 8/2016 | Silverman | G16H 50/50 |
| 2017/0039336 | A1* | 2/2017 | Bitran | H04B 1/385 |
| 2017/0039339 | A1* | 2/2017 | Bitran | G16H 40/67 |
| 2017/0039529 | A1* | 2/2017 | Reicher | G06Q 10/1095 |
| 2017/0124276 | A1* | 5/2017 | Tee | G06F 21/6245 |
| 2017/0185745 | A1* | 6/2017 | Wartski | G16H 20/13 |
| 2017/0209102 | A1* | 7/2017 | Parthasarathy | A61B 5/7275 |
| 2017/0221149 | A1* | 8/2017 | Hsu-Hoffman | G06Q 40/08 |
| 2017/0351832 | A1* | 12/2017 | Gahan | G16H 70/60 |
| 2017/0351834 | A1* | 12/2017 | Cahan | G16H 50/30 |
| 2017/0352119 | A1* | 12/2017 | Pittman | G16H 50/80 |
| 2018/0039752 | A1* | 2/2018 | Subbarao | G16H 40/67 |
| 2018/0144101 | A1* | 5/2018 | Bitran | G16H 40/20 |
| 2018/0150601 | A1* | 5/2018 | Astigarraga | G06Q 50/14 |
| 2019/0102670 | A1* | 4/2019 | Ceulemans | G06F 21/6218 |
| 2019/0114549 | A1* | 4/2019 | Olsher | G06Q 10/025 |
| 2019/0209806 | A1* | 7/2019 | Allen | G16H 20/70 |
| 2019/0228867 | A1* | 7/2019 | Smyth | G16H 80/00 |
| 2019/0252078 | A1* | 8/2019 | Schubert | G16H 10/60 |
| 2019/0272602 | A1* | 9/2019 | Ray | G06F 16/285 |
| 2019/0279069 | A1* | 9/2019 | Bastide | G16H 20/10 |

OTHER PUBLICATIONS

Mathew, P.S. et al. (Dec. 31, 2017 online). "Applications of IoT in Healthcare". In Cognitive Computing for Big Data Systems Over IoT (pp. 263-288). Springer, Cham., Lecture Notes on Data Engineering and Communications Technologies 14, DOI:10.1007/978-3-319-70688-7_11 (Year: 2017).*

Lee, E.K. et al. (Jul. 2017). "An interactive web-based decision support system for mass dispensing, emergency preparedness, and biosurveillance". In Proceedings of the 2017 International Conference on Digital Health (pp. 137-146). DOI:10.1145/3079452.3079473 (Year: 2017).*

Ahmed, M.N. et al. (Pub. May 15, 2017). "Cognitive computing and the future of health care cognitive computing and the future of healthcare: the cognitive power of IBM Watson has the potential to transform global personalized medicine". IEEE pulse, 8(3), 4-9. DOI: 10.1109/MPUL.2017.2678098 (Year: 2017).*

Chen, M. et al. (Pub. Mar. 15, 2018). "SPHA: Smart personal health advisor based on deep analytics". IEEE Communications Magazine, 56(3), 164-169. DOI: 10.1109/MCOM.2018.1700274 (Year: 2018).*

Kim, J., Lee, D., & Chung, K. Y. (Pub. online Nov. 22, 2011). "Item recommendation based on context-aware model for personalized u-healthcare service". Multimedia Tools and Applications, 71(2), 855-872. (Year: 2011).*

"WebMD Allergy," [online] WebMD © 2016, [retrieved Mar. 9, 2018], retrieved from the Internet: <https://itunes.apple.com/us/app/webmd-allergy/id588509171?mt=8>, 4 pg.

"Fact Sheet—Industry Statistics," [online] International Air Transport Association (IATA) Jun. 2017, retrieved from the Internet: <http://www.iata.org/pressroom/facts_figures/fact_sheets/Documents/fact-sheet-industryfacts.pdf>, 2 pg.

Safadi, G., "Allergy Pollen Count," [online] Dr. Safadi & Associates, Inc. [retrieved Mar. 9, 2018], retrieved from the Internet: <https://itunes.apple.com/us/app/allergy-pollen-count/id903685327?mt=8>, 4 pg.

Leggat, P., "Sources of health advice given to travelers," Journal of Travel Medicine, vol. 7, No. 2, Mar. 1, 2000, pp. 85-88.

Ryan, E.T. et al., "Health Advice and Immunizations for Travelers," [online] Massachusetts Medical Society © 2000, New England Journal of Medicine, vol. 342, No. 23, Jun. 8, 2000, pp. 1716-1725.

Hill, D.R., "Health problems in a large cohort of Americans traveling to developing countries," Journal of Travel, Medicine, vol. 7, No. 5, Sep. 1, 2000, pp. 259-266, retrieved from the Internet: <http://onlinelibrary.wiley.com/doi/10.2310/7060.2000.00075/full>, 2 pg.

Baxi, S.N. et al., "The role of allergen exposure and avoidance in asthma," Adolescent Medicine: State of the Art Reviews, vol. 21, No. 1, Apr. 21, 2010, p. 14.

* cited by examiner

TRAVEL HEALTH OPTIMIZATION SIMULATING HEALTH IMPACT OF INTENDED USER TRAVEL USING COGNITIVE ANALYTICS BASED ON CONDITIONS AT A GEOGRAPHIC LOCATION

BACKGROUND

The present invention relates to data processing systems.

The volume of personal and business travel continues to increase globally. Data processing systems commonly are used to schedule such travel. For example, traveler's oftentimes purchase airline tickets and reserve hotel accommodations using web based services hosted by data processing systems.

SUMMARY

A method includes determining an intent by a user to travel, identifying a geographic location to which the user intends to travel and identifying conditions at the geographic location, to which the user intends to travel, that impact health of human beings. The method also can include creating, using a processor, a health impact model for the user, the health impact model incorporating the identified conditions at the geographic location that impact health of human beings and the identified medical information pertaining to the user, the health impact model analyzing the determined conditions at the geographic location in a context of the accessed medical information pertaining to the user, and the health impact model determining an anticipated health impact on the user of the identified conditions at the geographic location based on the identified conditions at the geographic location and the identified medical information pertaining to the user. The method also can include, based on the analyzing by the health impact model, assigning a score to the anticipated health impact on the user of the identified conditions at the geographic location. The method also can include determining whether the score assigned to the anticipated health impact on the user of the identified conditions at the geographic location exceeds a threshold value. The method also can include, responsive to the score assigned to the anticipated health impact on the user of the identified conditions at the geographic location exceeding the threshold value, automatically initiating and controlling at least one action for the user.

A system includes a processor programmed to initiate executable operations. The executable operations include determining an intent by a user to travel, identifying a geographic location to which the user intends to travel and identifying conditions at the geographic location, to which the user intends to travel, that impact health of human beings. The executable operations also can include creating a health impact model for the user, the health impact model incorporating the identified conditions at the geographic location that impact health of human beings and the identified medical information pertaining to the user, the health impact model analyzing the determined conditions at the geographic location in a context of the accessed medical information pertaining to the user, and the health impact model determining an anticipated health impact on the user of the identified conditions at the geographic location based on the identified conditions at the geographic location and the identified medical information pertaining to the user. The executable operations also can include, based on the analyzing by the health impact model, assigning a score to the anticipated health impact on the user of the identified conditions at the geographic location. The executable operations also can include determining whether the score assigned to the anticipated health impact on the user of the identified conditions at the geographic location exceeds a threshold value. The executable operations also can include, responsive to the score assigned to the anticipated health impact on the user of the identified conditions at the geographic location exceeding the threshold value, automatically initiating and controlling at least one action for the user.

A computer program product includes a computer readable storage medium having program code stored thereon. The program code is executable by a data processing system to initiate operations. The operations include determining an intent by a user to travel, identifying a geographic location to which the user intends to travel and identifying conditions at the geographic location, to which the user intends to travel, that impact health of human beings. The operations also can include creating a health impact model for the user, the health impact model incorporating the identified conditions at the geographic location that impact health of human beings and the identified medical information pertaining to the user, the health impact model analyzing the determined conditions at the geographic location in a context of the accessed medical information pertaining to the user, and the health impact model determining an anticipated health impact on the user of the identified conditions at the geographic location based on the identified conditions at the geographic location and the identified medical information pertaining to the user. The operations also can include, based on the analyzing by the health impact model, assigning a score to the anticipated health impact on the user of the identified conditions at the geographic location. The operations also can include determining whether the score assigned to the anticipated health impact on the user of the identified conditions at the geographic location exceeds a threshold value. The operations also can include, responsive to the score assigned to the anticipated health impact on the user of the identified conditions at the geographic location exceeding the threshold value, automatically initiating and controlling at least one action for the user.

DETAILED DESCRIPTION

Figure 1:
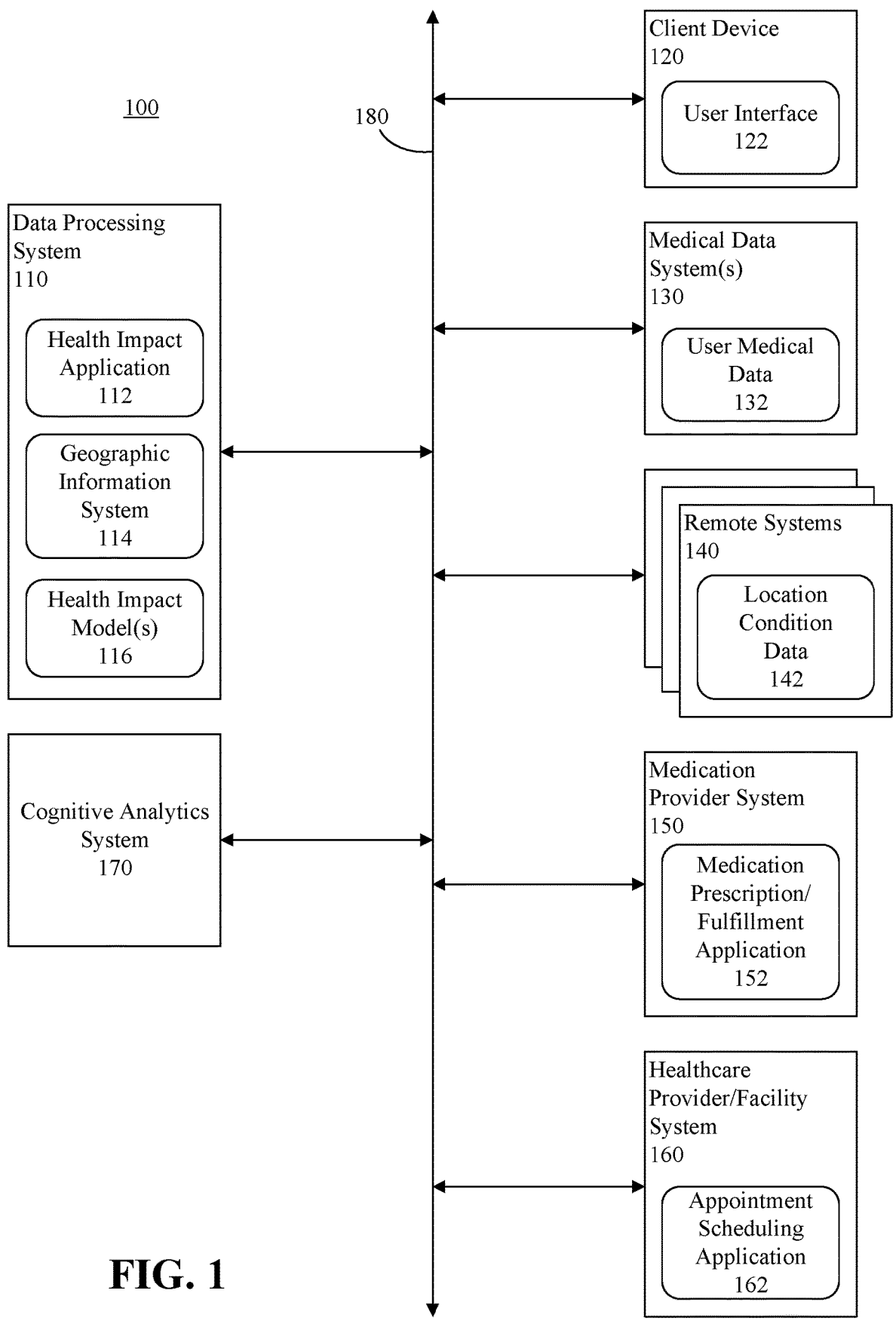
FIG. 1 is a block diagram illustrating an example of a computing environment.

This disclosure relates to data processing systems.

With the increase in personal and business travel, travelers are encountering many risks and factors which impact their health. The risks and factors are more important to the traveler when the traveler suffers medical conditions such as diabetes, pulmonary/respiratory issues and allergies. Further, when travelers are exposed to a destination's environmental risks, infectious diseases, injury or physiological challenges, these risks and factors are multiplied.

In accordance with the inventive arrangements disclosed herein, a geographic location to which a user intends to travel and medical information pertaining to the user can be identified. Conditions at the geographic location that impact health of human beings also can be identified. A health impact model can be created for the user, the health impact model analyzing the determined conditions at the geographic location in a context of the accessed medical information pertaining to the user. Based on analyzing by the health impact model, a score can be assigned to an anticipated health impact on the user of the identified conditions at the geographic location. If the score assigned to the anticipated health impact on the user of the identified conditions at the geographic location exceeds a threshold value, at least one action for the user can be automatically initiated and controlled.

Various actions that can be initiated and controlled include, but are not limited to, determining medication the user should take to alleviate or mitigate the anticipated health impact on the user, determining interactions of such medications with other medications the user may be taking or may be prescribed, automatically prescribing the medications, automatically scheduling the medications to be available for pickup or to be delivered to the user, etc. Other actions that can be initiated and controlled may include automatically scheduling an appointment for the user with a medical care provider (e.g., a medical care practitioner and/or medical care facility), communicating the user's medical data to the medical care provider, etc. The actions also may include automatically suggesting to the user alternative travel plans, or automatically scheduling alternative travel plans for the user.

Several definitions that apply throughout this document now will be presented.

As defined herein, the term "health impact model" means a computer-based model that simulates the health impact on a particular user of a condition that is present, or may be present, at a geographic location. In this regard, the health impact model is created for that particular user, and no other user. Other health impact models may be created for other users.

As defined herein, the term "condition" means a circumstance or factor that may affect the health of a user, and which may be incorporated into a health impact model to simulate the health impact of the condition on a particular user.

As defined herein, the term "geographic location" means a position on the earth specified by longitude and latitude, a name of a state, a name of a province, a name of a county, a name of a city or a name of a village. As the term "geographic location" is used herein, a specific building or structure is not a geographic location. In this regard, the term "geographic location," as defined herein, is an area larger than a single building or structure.

As defined herein, the term "responsive to" means responding or reacting readily to an action or event. Thus, if a second action is performed "responsive to" a first action, there is a causal relationship between an occurrence of the first action and an occurrence of the second action, and the term "responsive to" indicates such causal relationship.

As defined herein, the term "computer readable storage medium" means a storage medium that contains or stores program code for use by or in connection with an instruction execution system, apparatus, or device. As defined herein, a "computer readable storage medium" is not a transitory, propagating signal per se.

As defined herein, the term "data processing system" means one or more hardware systems configured to process data, each hardware system including at least one processor programmed to initiate executable operations and memory.

As defined herein, the term "processor" means at least one hardware circuit (e.g., an integrated circuit) configured to carry out instructions contained in program code. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "server" means a data processing system including at least one processor and memory configured to provide at least one shared service (e.g., data and resources) to a plurality of client devices. Network infrastructure, such as routers, firewalls, switches, access points and the like, are not servers as the term "server" is defined herein.

As defined herein, the term "client device" means a data processing system including at least one processor and memory that requests shared services from a server, and with which a user directly interacts. Examples of a client device include, but are not limited to, a workstation, a desktop computer, a computer terminal, a mobile computer, a laptop computer, a netbook computer, a tablet computer, a smart phone, a personal digital assistant, a smart watch, smart glasses, a gaming device, a set-top box, a smart television and the like. Network infrastructure, such as routers, firewalls, switches, access points and the like, are not client devices as the term "client device" is defined herein.

As defined herein, the term "real time" means a level of processing responsiveness that a user or system senses as sufficiently immediate for a particular process or determination to be made, or that enables the processor to keep up with some external process.

As defined herein, the term "output" means storing in memory elements, writing to display or other peripheral output device, sending or transmitting to another system, exporting, or similar operations.

As defined herein, the term "automatically" means without user intervention.

As defined herein, the term "user" means a person (i.e., a human being).

FIG. 1 is a block diagram illustrating an example of a computing environment 100. The computing environment 100 can include a data processing system 110, a client device 120, a medical data system 130, and one or more remote systems 140. The computing environment 100 also may include a medication provider system 150 and/or a healthcare provider/facility system 160. The computing environment 100 further may include a cognitive analytics system 170, which is a data processing system configured to use artificial intelligence (e.g., machine learning) to analyze data. The cognitive analytics system 170 can source big data to use in performing analytics, adapting to different contexts in real time, or near real time. Big data includes extremely large data sets that may be analyzed computationally to reveal patterns, trends, and associations. An example of the cognitive analytics system 170 is IBM® Watson Health™, although the present arrangements are not limited in this regard.

The data processing system 110 can be communicatively linked to the client device 120, the medical data system 130, the one or more remote systems 140, the medication provider system 150, the healthcare provider/facility system 160, and the cognitive analytics system 170 via at least one communication network 180. The communication network 180 is the medium used to provide communications links between various devices and systems connected together within the computing environment 100. The communication network 180 may include connections, such as wire, wireless communication links, or fiber optic cables. The communication network 180 can be implemented as, or include, any of a variety of different communication technologies such as a wide area network (WAN), a local area network (LAN), a wireless network, a mobile network, a Virtual Private Network (VPN), the Internet, the Public Switched Telephone Network (PSTN), or similar technologies.

The data processing system 110 can host a health impact application 112 configured to initiate and control at least one action for a user of the client device 120, as will be described herein. The data processing system 110 also can host a geographic information system 114 configured to provide geographic information for various geographic locations, or the geographic information system 114 can be hosted by another system accessible by the data processing system 110. In one non-limiting arrangement, the health impact application 112 and, optionally, the geographic information system 114 can be components of a system with which users interact with to schedule travel, for example to reserve airline tickets, reserve passage on cruise ships, reserve hotel rooms, etc. In another non-limiting arrangement, rather than executing on the data processing system 110, the health impact application 112 and/or geographic information system 114 can be hosted on, and execute on, the client device 120. The health impact application 112 can be configured to create health impact models 116, as will be described herein.

For simplicity, in the following description reference will be made to arrangements in which the health impact application 112 and geographic information system 114 execute on the data processing system 110 to provide services to client devices, including the client device 120, but it will be understood by those skilled in the art that the health impact application 112 and/or geographic information system 114 may instead execute on the client device 120, and/or the geographic information system 114 may execute on a system accessible by the data processing system 110 and/or the client device 120.

The client device 120 can present a user interface 122 via which the user can interact with the client device 120 and utilize the health impact application 112. In one arrangement, the user interface 122 can be provided by the health impact application 112 to the client device 120, for example to a web browser or mobile application executing on the client device 120. In such arrangement, the web browser or mobile application can receive the user interface 122 from the health impact application 112 via the communication network 180 and present the user interface 122 to the user, for example via a display. In another arrangement, the user interface 122 can be hosted natively on the client device 120. For example, an application or mobile application executing on the client device 120 can include the user interface 122 can present the user interface 122 to the user, for example via the display. In an arrangement in which the health impact application 112 executes on the client device 120, the health impact application 112 can present the user interface 122 to the user, for example via the display.

The medical data system(s) 130 can store user medical data 132, for example in one or more data tables. The data tables can be contained in one or more databases hosted by the medical data system(s) 130. The user medical data 132 can include, for example, a user profile of the user, a medical profile of the user, and other medical information for the user. The user profile of the user can indicate the user's contact information, gender, age, address, occupation, place of employment, travel history, etc. The medical profile of the user can indicate ailments/diseases/symptoms currently afflicting the user and/or ailments/diseases/symptoms which previously have afflicted the user, as well as information indicating the user's general health (e.g., height, weight, body mass index, blood pressure, resting heart rate, etc.). The medical profile also can indicate medications currently prescribed to the user and medications previously prescribed to the user. The medical profile also can indicate various medical treatments that have been prescribed to the user and/or performed on the user, etc. The other medical information can indicate the user's primary care physician(s), other physicians who have treated the user, contact information for the physicians, and so on. The health impact application 112 can access the user medical data 132 from the medical data system(s) 130.

The remote systems 140 can store location condition data 142 for various geographic locations. The remote systems 140 can include, but are not limited to, weather information systems, pollution information systems, systems that track diseases (e.g., disease outbreaks), news information systems, systems that host social networking services, etc. The location condition data 142 can indicate conditions at various geographic locations that impact health of human beings, such as altitude, weather conditions, ozone levels, pollution conditions, allergens present, diseases present, disease outbreaks, severity of pollutions, severity of allergens, severity of diseases, health warnings, boil water advisories, water line breaks, flooding, earthquake warnings, and so on. The location condition data 142 also can include predicted condition data, for example predicted condition data for one or more days, weeks, months or years in the future. The health impact application 112 can access the location condition data 142 from the remote system(s) 140.

The medication provider system 150 can host a medication prescription/fulfillment application 152. The medication prescription/fulfillment application 152 can receive medication prescriptions and/or medication fulfillment requests and schedule for delivery of the medication(s) to users and/or schedule for the medication(s) to be available for pickup by the users. For example, the medication prescription/fulfillment application 152 can interface with data processing systems at various pharmacies and/or other medication dispensaries to schedule delivery of the medications by the pharmacies and/or other medication dispensaries, or to schedule pickup of the medications at the pharmacies and/or other medication dispensaries. In illustration, a physician can access the medication prescription/fulfillment application 152 to provide a prescription for the user to the medication prescription/fulfillment application 152. The medication prescription/fulfillment application 152 can automatically communicate the prescription to the health impact application 112, which can select a pharmacy or other medication dispensary to fill the prescription based on the user's travel plans.

The healthcare provider/facility system 160 can host an appointment scheduling application 162. The appointment scheduling application 162 can automatically schedule appointments for users with healthcare providers and/or healthcare facilities at the behest of the health impact application 112 based on the user's travel plans.

Figure 2:
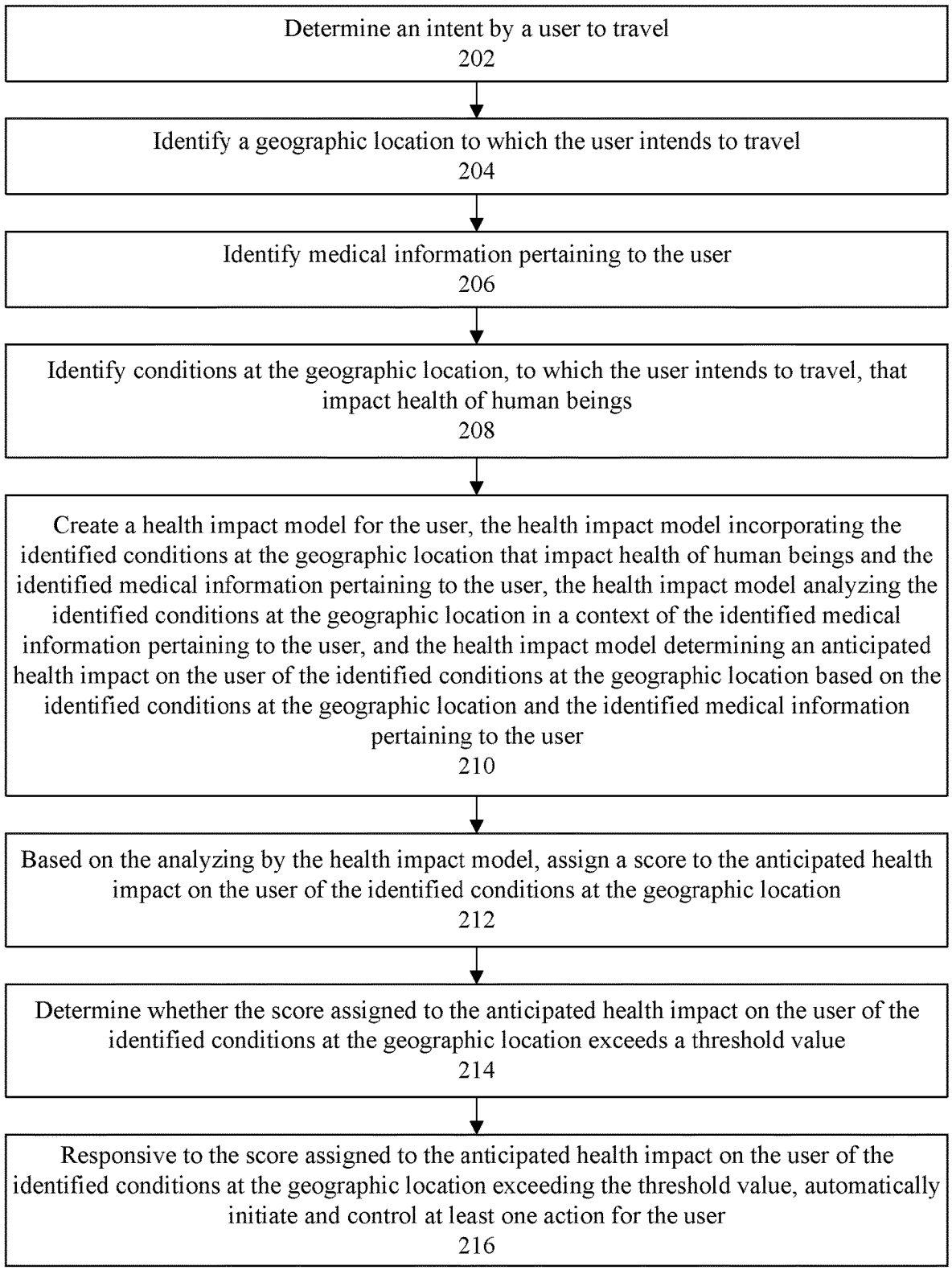
FIG. 2 is a flowchart illustrating an example of a method of initiating at least one action for a user intending to travel.

FIG. 2 is a flowchart illustrating an example of a method 200 of initiating at least one action for a user intending to travel. The method 200 can be implemented by the health impact application 112. In the following description, reference will be made both to FIG. 1 and to FIG. 2.

At step 202, the health impact application 112 can determine an intent by a user to travel. At step 204, the health impact application 112 can identify a geographic location to which the user intends to travel. In one non-limiting arrangement, the health impact application 112 can access travel records of the user, for example from a user profile of the user, and determine whether geographic location is a location to which the user does not normally travel or does not frequently travel. In illustration, responsive to identifying the geographic location at step 204, the health impact application 112 can determine whether the user has traveled to the geographic location a threshold number of times over a past time frame (e.g., past three months, past six months, past year, past two years, etc.) If the user normally or frequently travels to the geographic location, the process can end after step 204. If, however, the user does not normally or frequently travel to the geographic location, the process can proceed to step 206. At step 206, the health impact application 112 can identify medical information pertaining to the user.

In illustration, referring to steps 202-206, using the client device 120, the user can access the health impact application 112 and, via the client device 120, the health impact application 112 can present to the user the user interface 122. The user interface 122 can present a plurality of fields in which the user can enter various information. The user can enter information into the fields and/or select information from user selectable menu items associated with the fields.

By way of example, the user can enter, into the user interface 122, information including a user identifier, a geographic location from which the user will begin travel, the geographic location to which the user intends to travel, and travel dates. The user can indicate the geographic locations by entering names of the geographic locations (e.g., country, state, province, county, city, village, etc., or section thereof), or by entering Global Positioning System (GPS) coordinates of the geographic locations. In the case that the user enters the name of the geographic locations, the health impact application 112 can determine the GPS coordinates of the geographic locations using the geographic information system 114. In the case that the user enters the GPS coordinates, the health impact application 112 can determine the name of the geographic locations using the geographic information system 114. The user also can enter information specifying a preferred means of travel (e.g., air, train, cruise ship, etc.), a preferred travel provider (e.g., airline, rail line, cruise company, etc.), travel rewards the user may have accumulated, a hotel where the user will be staying or desires to stay, a desired type of hotel, a desired location of the hotel, etc.

Via the user interface 122, the health impact application 112 can prompt the user to indicate an authorization for the health impact application 112 to access medical information pertaining to the user. In response to the prompt, the user can enter, into the user interface 122, a user security information (e.g., user identifier, password, personal identification number (PIN) and/or or other security data) required to access the user's medical information (e.g., user medical data 132). If the user's medical information is stored in a particular medical data system 130, the user can input information indicating that particular medical data system 130. For instance, the user can select the particular medical data system 130 from a list of medical data systems 130 presented by the user interface 122. The health impact application 112 can access the user medical data 132 for the user from the medical data system(s) 130 using the provided user security information. In a further arrangement, the health impact application 112 can access the user security information from a user profile assigned to the user, and access the user medical data 132 for the user from the medical data system(s) 130 using the user security information accessed from the user profile. In another arrangement, the user can enter the medical information via the user interface 122. For example, the user interface 122 can present fields in which the user can enter the user's medical information, and/or menus from which the user can select information corresponding to the user's medical information.

In another aspect of the present arrangements, the health impact application 112 can determine the intent by the user travel and identify the geographic location to which user intents to travel by analyzing one or more electronic messages communicated by, or to, the user. Such an electronic message can be an e-mail, an instant message, a post in a social networking system, or the like. In illustration, the user can communicate an electronic message to the health impact application 112, or the health impact application 112 can monitor electronic messages communicated by, or to, the user. By way of example, the health impact application 112 can identify the user based on a user identifier of the user contained in the electronic message (e.g., in a header of the electronic message, in a body of the electronic message, or in a document attached to the electronic message). Further, the electronic message can include the user's travel itinerary, and the health impact application 112 can perform natural language processing (NLP) and semantic analysis, which are known in the art, on content of the e-mail and, based on the content, determine the intent by the user travel and identify the geographic location to which user intents to travel. Based on the user identifier, the health impact application 112 can identify a user profile of the user and, using security information provided in the user profile, identify medical information pertaining to the user.

In another aspect of the present arrangements, the health impact application 112 can determine the intent by the user travel and identify the geographic location to which user intents to travel by analyzing an electronic calendaring system used by the user. For instance, the health impact application 112 can monitor an electronic calendar of the user, and identify travel destinations and dates of travel by analyzing the electronic calendar. Again, the health impact application 112 can implement NLP to identify travel destinations indicated in the electronic calendar. Based on the user identifier to which the electronic calendar is assigned, the health impact application 112 can identify a user profile of the user and, using security information provided in the user profile, identify medical information pertaining to the user.

At step 208, the health impact application 112 can identify conditions at the geographic location, to which the user intends to travel, that impact the health of human beings. In illustration, the health impact application 112 can automatically search the remote systems 140 for location condition data 142 for the geographic location. By way of example, the health impact application 112 can automatically generate search queries, and communicate the search queries to the remote systems 140. In response to the search queries, the remote systems 140 can communicate to the health impact application 112 location condition data 142 discovered using the search queries.

The search queries can include as a search term a name or geographic coordinates of the geographic location to which the user intents to travel. The search queries also can specify dates the user is expected to be at the geographic location, which can be determined based on the user's intended dates of travel. The search queries also can specify that location condition data 142 is to be accessed.

In one non-limiting arrangement, the search queries further can specify the types of the location condition data 142 to be accessed. For instance, based on the user medical data 132 for the user, the health impact application 112 can determine types of location condition data 142 that may be of significance to the user's health, and construct the search queries to search for those types of location condition data 142. For example, if the user medical data 132 for the user indicates that the user is afflicted with asthma or a chronic obstructive pulmonary disease (COPD), the health impact application 112 can determine types of location condition data 142 that represent conditions that have a health impact on asthma or COPD, such as altitude, ozone levels, pollen counts, level of atmospheric pollution, weather conditions, health warnings from one or more health agencies (e.g., the Centers for Disease Control and Prevention (CDC) agency), etc., and construct the search queries to search for those types of location condition data 142. In another example, if the user medical data 132 for the user indicates that the user suffers from an immune deficiency (e.g., Acquired Immune Deficiency Syndrome), the health impact application 112 can determine types of location condition data 142 that represent conditions that have a health impact on people that suffer from immune deficiency, such as bacterial and or viral levels/outbreaks, health warnings from one or more health agencies, etc., and construct the search queries to search for those types of location condition data 142. Still, the health impact application 112 can determine any other types of location condition data 142 that may be of significance to the user's health, and construct the queries to search for such location condition data 142, and the present arrangements are not limited in this regard.

In one aspect of the present arrangements, the health impact application 112 can compare the location condition data 142 for the geographic location to which the user intends to travel to location condition data 142 for the user's current geographic location. If results from the comparison indicate that the location condition data 142 for the intended geographic location and the current geographic location do not differ by at least a threshold amount, the process can end after step 208. If the difference is greater than the threshold amount, the process can proceed to step 210.

At step 210, the health impact application 112 can create a health impact model 116 for the user. The health impact model 116 can incorporate the identified conditions at the geographic location, to which the user intends to travel, that impact health of human beings (e.g., the location condition data 142, or a subset of the location condition data 142 specified by the search queries). The health impact model 116 also can incorporate the identified medical information pertaining to the user (e.g., the user medical data 132). The health impact model 116 can analyze the identified conditions at the geographic location in a context of the identified medical information pertaining to the user. Further, health impact model 116 can determine an anticipated health impact on the user of the identified conditions at the geographic location based on the identified conditions at the geographic location and the identified medical information pertaining to the user.

The health impact model 116 can include features such as demographic data, data representing a medical event (e.g., sudden attack onset of Asthma), data representing medical devices, data representing medications, data representing medical treatment, data representing geographic information, and data representing corresponding outcomes related to geography. The data can be combined into the health impact model 116 using regression analysis or feature clustering such that an event and geographical data may be processed in combination with a specific user's demographic data to predict the likelihood of a future adverse health impact (e.g., an adverse medical event).

In illustration, the health impact model 116 can identify in the user medical data 132 ailments/diseases/symptoms currently afflicting the user and/or ailments/diseases/symptoms which previously have afflicted the user, and identify conditions at the geographic location that may or will impact such ailments/diseases/symptoms. Further, the health impact model 116 can analyze the conditions at the geographic location in context of the user's ailments/diseases/symptoms to determine a nature of impact (e.g., ailments/diseases/symptoms that will be aggravated) and a level of impact (e.g., a level of severity of the aggravation) the conditions at the geographic location may or will have on the user given the user's ailments/diseases/symptoms and the user's general health.

In one non-limiting arrangement, the health impact model 116 can interface with the cognitive analytics system 170 to perform the analysis. In illustration, the health impact model 116 can, via the communication network 180, input into the cognitive analytics system 170 parameters representing the ailments/diseases/symptoms/health, parameters representing the conditions at the geographic location, and parameters representing the user's anticipated stay at the geographic location (e.g., dates, times, areas to be visited, etc.). In an aspect, the health impact model 116 can filter information representing and/or related to the ailments/diseases/symptoms and/or conditions at the geographic location and generate parameters for information that is determined by the health impact model 116 to be of highest significance toward analyzing the health impact on the user, and the health impact model 116 can communicate those parameters to the cognitive analytics system 170. In another aspect, the health impact model 116 can generate parameters for all identified ailments/diseases/symptoms of the user and/or conditions at the geographic location, and the health impact model 116 can communicate those parameters to the cognitive analytics system 170.

The cognitive analytics system 170 can perform cognitive analytics using the provided parameters to analyze the conditions at the geographic location in context of the user's ailments/diseases/symptoms/health to determine the nature of impact and level of impact the conditions at the geographic location may or will have on the user's health given the user's ailments/diseases/symptoms and the user's general health. The cognitive analytics system 170 can generate data indicating the nature of the impact and the level of impact, and communicate such data to the health impact model 116 and/or the health impact application 112. In illustration, the cognitive analytics system 170 can process historical data for other users having ailments/diseases/symptoms and/or general health similar to the user who have been exposed to conditions similar to those determined for the geographic location, identify adverse health impacts such conditions have had on the other users, and identify remedies that have been used to treat the adverse health impacts. The health impact application 112 can incorporate such information into the health impact model 116 created for the user. The impact may be presented as a percentage or intensity of likelihood. For instance, if assume that the user is an asthmatic, and is traveling to Los Angeles in Summer. The health impact model 116 can include features which indicate adverse health related/medical events for asthmatics in Los Angeles, and the health impact model 116 can indicate a high likelihood of adverse health related issues for the user. Results generated from the health impact model 116 can may be presented in the user interface 122 as a sliding indicator, an intensity scale, or a weather-related indicator. Future weather data also may be incorporated into the health impact model 116 and analyzed to generate the results.

In an arrangement in which the user has indicated a hotel where the user will be staying, or where the user desires to stay, the health impact application 112 can include in the health impact model 116, and parameters generated by the health impact model 116, information pertaining to the hotel, for example a location of the hotel, a structural layout of the hotel, and/or location condition data 142 related to the hotel. The location condition data 142 related to the hotel can include, for example, information from social media services or other remote systems 140 indicating occurrences of illness of people staying in the hotel, occurrences of structural problems (e.g., water line breaks, sewage line breaks, mold in the hotel, etc.), and other location condition data 142 pertaining to the hotel that may impact the health of user if the user were to stay in or visit the hotel. In an arrangement in which the health impact application 112 will be used in a process to generate recommendations of hotels for the user to stay, the health impact application 112 can include in the health impact model 116 information pertaining to hotels that may be considered by the user to stay while visiting the intended geographic location.

At step 212, the health impact application 112 can, based on the analyzing by the health impact model 116, assign a score to the anticipated health impact on the user of the identified conditions at the geographic location. A low score can indicate little to no anticipated negative health impact on the user. A high score can indicate that a negative health impact on the user is anticipated, for example if the user does not take precautionary measures, such as getting vaccinated, taking medication, avoiding certain areas of the geographic location, etc. At step 214, the health impact application 112 can determine whether the score assigned to the anticipated health impact on the user of the identified conditions at the geographic location exceeds a threshold value.

At step 216, the health impact application 112 can, responsive to the score assigned to the anticipated health impact on the user of the identified conditions at the geographic location exceeding the threshold value, automatically initiate and control at least one action for the user. An example of such an action can include determining a recommended course of action for the user and communicating to the user an electronic message recommending that course of action to be taken by the user. For instance, the health impact application 112 can determine the user should consider rescheduling the travel or changing the travel to another geographic location, and communicate an electronic message to the user and/or the user's travel agent recommending such. In one non-limiting arrangement, the health impact application 112 can automatically schedule alternative travel plans for the user. For example, the health impact application 112 can automatically schedule the user's travel for a time when the conditions that will adversely impact the user's health are expected to subside, or select an alternative destination. For instance, if the user is scheduling travel to a particular office of a company in a geographic location, the health impact application 112 can identify another office of that company near that particular office, but in another geographic location, and having conditions that are less severe with regard to the impact on the health of the user. The health impact application 112 automatically schedule travel of the user to the other office, for example by interfacing with a travel planning/scheduling system.

In one aspect, the health impact application 112 can warn a travel agency or downstream parties that the traveler has a medical condition and would suffer an adverse health impact if visiting the intended geographic location. Further, the health impact application 112 can contact a medical practitioner and/or travel agent for advisement relating to the anticipated impact of the identified conditions at the geographic location on the user, for example by communicating an electronic message to the medical practitioner and/or travel agent. The electronic message can include a hyperlink to a webpage where the medical practitioner and/or travel agent can provide advisement information. Responsive to receiving the advisement via the webpage, the health impact application 112 can communicate the advisement information to the user, for example in an electronic message. In another arrangement, the health impact application 112 can communicate to the user an electronic message suggesting that the user access the webpage to view the advisement information.

In another example, if the user suffers from a medical condition (e.g., allergies or asthma), and is scheduled to travel by car, bus or train through a region having conditions that will have an adverse impact on the medical condition (e.g., high pollen counts and/or pollution in the air during the user's travel), the health impact application 112 can recommend an alternate travel route to avoid that region and travel through a different region having conditions that will have less of an adverse impact on the medical condition (e.g., less pollen and/or pollution in the air). Further, the health impact application 112 can receive travel updates, in real time, from a GPS device used by the user for navigation, such as the user's smart phone. In illustration, if the user enters a destination into the smart phone's GPS system, and a mapping application suggests a route that will take the user through a region that will have high pollen counts (e.g., a high count of a specific type of pollen the user should avoid) and/or pollution in the air during the user's travel, the health impact application 112 can communicate an electronic message to the user recommending that the user take an alternate route. In one aspect, the health impact application 112 can communicate data to the smart phone's GPS system requesting the GPS system select an alternate route, and recommending a route that will take the user through a region having lower pollen count (e.g., a lower count on the specific type of pollen the user should avoid) and/or pollution. In this regard, the health impact application 112 can interface with the geographic information system 114 (or other mapping system) to determine possible routes to take the user to the intended destination, evaluate the conditions along the possible routes, and select a route that will have the lowest adverse health impact on the user. The health impact application 112 can recommend the selected route to the user's GPS device, which can re-route the user's directions accordingly.

The health impact application 112 also can recommend to the user to consult a medical practitioner, and communicate an electronic message to the user recommending that the user consult a medical practitioner. In another instance, the health impact application 112 can determine the user should take a particular medication, a particular type of medication, or types of medications to mitigate the anticipated health impact on the user, as well as a schedule for taking the medication, and communicate an electronic message to the user recommending that the user take the medication at the determined schedule. For example, the health impact application 112 can interface with the cognitive analytics system 170, which can analyze data provided by the health impact application 112 and, based on such analysis, determine medication(s) that will alleviate or mitigate the anticipated health impact on the user of the conditions at the geographic location. Further, the cognitive analytics system 170 can determine an anticipated impact of the determined medication(s) at alleviating or mitigating the anticipated health impact on the user of the identified conditions at the geographic location by performing an analysis of the medication(s) in a context of the identified conditions at the geographic location and the user medical data 132 pertaining to the user. The cognitive analytics system 170 can communicate to the health impact application 112 a listing of the determined medication(s) and the anticipated impact of the determined medication(s). In turn, the health impact application 112 can communicate to the user such information.

Further, the cognitive analytics system 170 can determine whether there are any medication interactions between any of the determined medications, and avoid recommending multiple medications that may result in adverse interactions. Further, the health impact application 112 can identify, from the user medical data 132 of the user, which medications the user may already be taking, and communicate a listing of such medications to the cognitive analytics system 170. The cognitive analytics system 170 can determine whether there are any medication interactions between any of the determined medications and the medications the user already is taking, and avoid recommending medications that may result in adverse interactions with the medications the user already is taking. Further, the cognitive analytics system 170 can determine possible side effects of taking the recommended medications, and communicate information regarding the side effects to the health impact application 112. The health impact application 112 can communicate such information to the user, for example in an electronic message.

Another example of an action that can be initiated and controlled by the health impact application 112 is to schedule for fulfillment of a medication prescription for the user (e.g., the medication(s) selected to alleviate or mitigate the anticipated heath impact on the user of the identified conditions at the geographic location), and schedule for delivery of the medication or for pickup of the medication from a medication provider (e.g., a pharmacy). By way of example, the health impact application 112 can generate a prescription for medication for the user, identify a prescription for medication in the user medical data 132, or receive a medical prescription from a medical practitioner who treats the user. The health impact application 112 can communicate the prescription to the medical prescription/fulfillment application 152 of a medication provider. Further, the health impact application 112 can, via the medical prescription/fulfillment application 152, schedule for the prescribed medication to be delivered to the user or to be picked up by the user. In one aspect, the health impact application 112 can receive from the client device 120 of the user information indicating the user's current geographic location (e.g., GPS coordinates) and select a medication provider within a threshold distance of that geographic location. In another aspect, the health impact application 112 can access electronic calendar information for the user from an electronic calendar used by, or assigned to, the user, travel information for the user stored by a travel scheduling system, or other information related to the user to determine an expected geographic location of the user at a particular time/day, and select a medication provider within a threshold distance of that geographic location. In yet another aspect, the health impact application 112 can access the user medical data 132 of the user to identify one or more medication providers indicated in the user medical data 132, and select the medication provider from the user medical data 132 of the user.

The health impact application 112 also can determine precautions that should be observed by the Examiner, and communicate a list of the precautions in the electronic message. In another example, the health impact application 112 can integrate with one or more medical alert systems, and via the medical alert system(s), communicate to the user a list of precautions the user should observe when traveling to the geographic location. For instance, if the user suffers from asthma, the health impact application 112 can indicate to the user to avoid outdoor activities due to pollutions in the air, indicate areas at the geographic location to be avoided by the user (e.g., areas with high pollen count, dust, smog, etc.), and so on.

The health impact application 112 also can communicate to the user, for example in the electronic message, a list of services offered at medical centers at or near the geographic location to which the user intends to travel. The health impact application 112 can include with the list the addresses of the medical centers, contact information for the medical centers (e.g., telephone numbers, contact names, etc.), and so on.

Another example of an action that can be initiated and controlled by the health impact application 112 is to automatically schedule an appointment for the user with a medical care provider, for example by interfacing with the appointment scheduling application 162. Responsive to the health impact application 112 scheduling the appointment, the health impact application 112 and/or the appointment scheduling application 162 can communicate to the user an electronic message indicating that the appointment has been scheduled and indicating a time/day of the appointment. Further, responsive to the health impact application 112 scheduling the appointment, the health impact application 112 can automatically notify the medical care provider of the identified anticipated health on the user impact of the identified conditions at the geographic location. For example, the health impact application 112 can communicate an electronic message with such information to the health care provider and/or communicate such information to the appointment scheduling application 162.

In one aspect, the health impact application 112 can receive from the client device 120 of the user information indicating the user's current geographic location (e.g., GPS coordinates) and select a medical care provider within a threshold distance of that geographic location. In another aspect, the health impact application 112 can access electronic calendar information for the user, travel information for the user stored by a travel scheduling system, or other information related to the user to determine an expected geographic location of the user at a particular time/day, and select a medical care provider within a threshold distance of that geographic location. In yet another aspect, the health impact application 112 can access the user medical data 132 of the user to identify one or more medical care providers indicated in the user medical data 132, and select the medical care provider from the user medical data 132 of the user. Further, the health impact application 112 can cache the user medical data 132 of the user and communicate the user medical data 132 of the user to the medical care provider in response to scheduling the appointment for the user.

Further, the health impact application 112 can prepare for a worst-case scenario, and maintain the health impact model 116. Thus, if the health impact application 112 detects changes to the user's travel plans and/or changes in conditions at the geographic location, the health impact application 112 can implement processes in real time to initiate and control further actions that may be warranted due to the changes. The health impact application 112 also can implement a personal medical emergency plan for the user, for example by automatically transferring user medical data 132 for the user to any medical center across the globe. Further, the health impact application 112 can locate and suggest certain types of medical staff if the user may need special types of treatment and/or medications.

Figure 3:
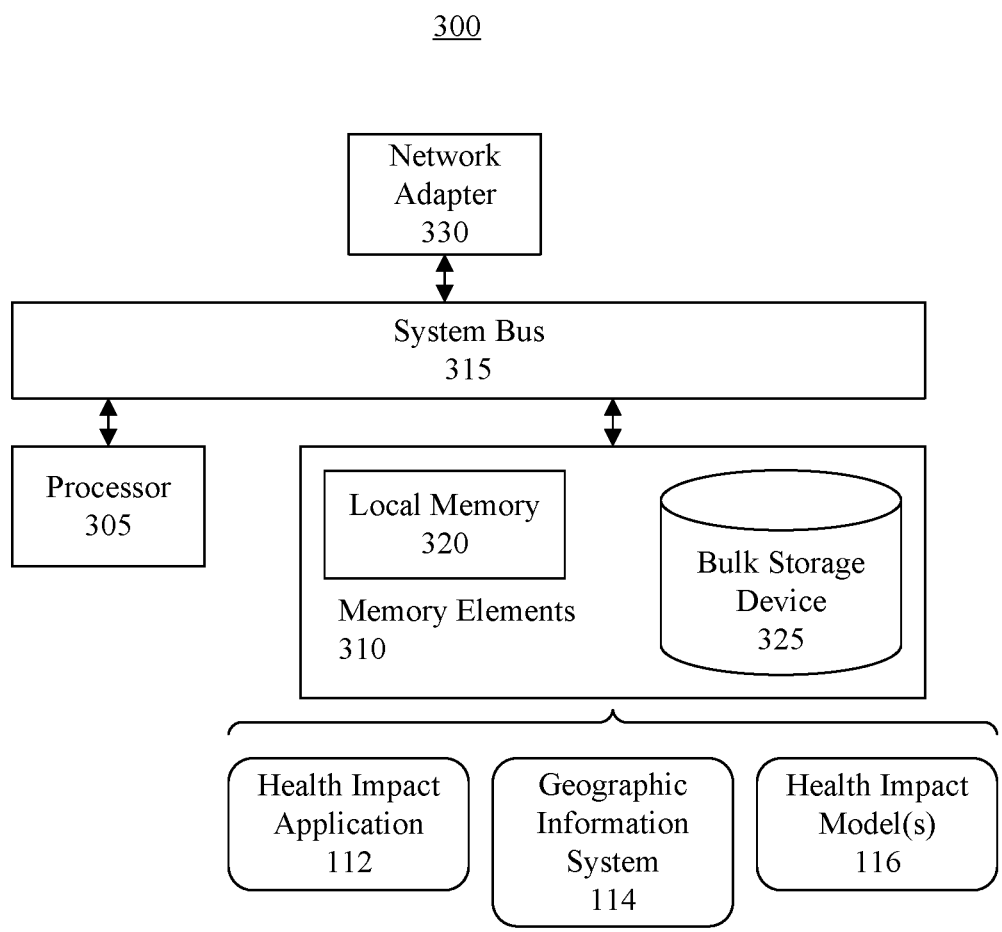
FIG. 3 is a block diagram illustrating example architecture for a data processing system.

FIG. 3 depicts a block diagram of a data processing system 110 configured to automatically initiate and control at least one action for a user in accordance with an arrangement disclosed within this specification.

The data processing system 110 can include at least one processor 305 (e.g., a central processing unit) coupled to memory elements 310 through a system bus 315 or other suitable circuitry. As such, the data processing system 110 can store program code within the memory elements 310. The processor 305 can execute the program code accessed from the memory elements 310 via the system bus 315. It should be appreciated that the data processing system 110 can be implemented in the form of any system including a processor and memory that is capable of performing the functions and/or operations described within this specification. For example, the data processing system 110 can be implemented as a server, a plurality of communicatively linked servers, a workstation, a desktop computer, and so on.

The memory elements 310 can include one or more physical memory devices such as, for example, local memory 320 and one or more bulk storage devices 325. Local memory 320 refers to random access memory (RAM) or other non-persistent memory device(s) generally used during actual execution of the program code. The bulk storage device(s) 325 can be implemented as a hard disk drive (HDD), solid state drive (SSD), or other persistent data storage device. The data processing system 110 also can include one or more cache memories (not shown) that provide temporary storage of at least some program code in order to reduce the number of times program code must be retrieved from the bulk storage device 325 during execution.

One or more network adapters 330 can be coupled to data processing system 110 to enable the data processing system 110 to become coupled to other systems, computer systems, remote printers, and/or remote storage devices through intervening private or public networks. Modems, cable modems, transceivers, and Ethernet cards are examples of different types of network adapters 330 that can be used with the data processing system 110.

As pictured in FIG. 3, the memory elements 310 can store the components of the data processing system 110 of FIG. 1, namely the health impact application 112 and, optionally, the geographic information system 114. Being implemented in the form of executable program code, these components of the data processing system 110 can be executed by the data processing system 110 and, as such, can be considered part of the data processing system 110. Further, the memory elements 310 can store the health impact model(s) 116 created by the data processing system 110. Moreover, health impact application 112, geographic information system 114 and health impact model(s) 116 are functional data structures that impart functionality when employed as part of the data processing system 110.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

For purposes of simplicity and clarity of illustration, elements shown in the figures have not necessarily been drawn to scale. For example, the dimensions of some of the elements may be exaggerated relative to other elements for clarity. Further, where considered appropriate, reference numbers are repeated among the figures to indicate corresponding, analogous, or like features.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart(s) and block diagram(s) in the Figures illustrate the architecture, functionality, and operation of possible implementations of systems, methods, and computer program products according to various embodiments of the present invention. In this regard, each block in the flowchart(s) or block diagram(s) may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "includes," "including," "comprises," and/or "comprising," when used in this disclosure, specify the presence of stated features, integers, steps, operations, elements, and/or components, but do not preclude the presence or addition of one or more other features, integers, steps, operations, elements, components, and/or groups thereof.

Reference throughout this disclosure to "one embodiment," "an embodiment," "one arrangement," "an arrangement," "one aspect," "an aspect," or similar language means that a particular feature, structure, or characteristic described in connection with the embodiment is included in at least one embodiment described within this disclosure. Thus, appearances of the phrases "one embodiment," "an embodiment," "one arrangement," "an arrangement," "one aspect," "an aspect," and similar language throughout this disclosure may, but do not necessarily, all refer to the same embodiment.

The term "plurality," as used herein, is defined as two or more than two. The term "another," as used herein, is defined as at least a second or more. The term "coupled," as used herein, is defined as connected, whether directly without any intervening elements or indirectly with one or more intervening elements, unless otherwise indicated. Two elements also can be coupled mechanically, electrically, or communicatively linked through a communication channel, pathway, network, or system. The term "and/or" as used herein refers to and encompasses any and all possible combinations of one or more of the associated listed items. It will also be understood that, although the terms first, second, etc. may be used herein to describe various elements, these elements should not be limited by these terms, as these terms are only used to distinguish one element from another unless stated otherwise or the context indicates otherwise.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
    determining an intent by a user to travel;
    identifying a geographic location to which the user intends to travel;
    identifying medical information pertaining to the user;
    identifying conditions at the geographic location, to which the user intends to travel, that impact health of human beings;
    creating, using a processor, a health impact model for the user, the health impact model comprising a plurality of different types of data, wherein the data is combined into the health impact model using regression analysis or feature clustering, and the health impact model incorporating the identified conditions at the geographic location that impact health of human beings and the identified medical information pertaining to the user, the health impact model analyzing the identified conditions at the geographic location in a context of the identified medical information pertaining to the user, and the health impact model determining an anticipated health impact on the user of the identified conditions at the geographic location based on the identified conditions at the geographic location, the identified medical information pertaining to the user by simulating the health impact of the identified conditions on the user using a cognitive analytics system;
    based on the analyzing by the health impact model, assigning a score to the anticipated health impact on the user of the identified conditions at the geographic location;
    determining whether the score assigned to the anticipated health impact on the user of the identified conditions at the geographic location exceeds a threshold value; and
    responsive to the score assigned to the anticipated health impact on the user of the identified conditions at the geographic location exceeding the threshold value, automatically communicating an electronic message to a medical practitioner, the electronic message comprising a hyperlink to a webpage where the medical practitioner provides advisement information, receiving via the webpage the advisement information from the medical practitioner, and communicating to the user an electronic message comprising the advisement information.

2. The method of claim 1, further comprising:
    determining whether the geographic location is a location where the user has traveled to at least a threshold number of times over a past particular time frame;
    wherein the identifying the conditions at the geographic location is responsive to determining that the location is not where the user has traveled to at least the threshold number of times over the past particular time frame.

3. The method of claim 1, further comprising:
    responsive to the score assigned to the anticipated health impact on the user of the identified conditions at the geographic location exceeding the threshold value, determining an anticipated impact of at least one medication at alleviating or mitigating the anticipated health impact on the user of the identified conditions at the geographic location by performing an analysis of the at least one medication in a context of the identified conditions at the geographic location and the medical information pertaining to the user.

4. The method of claim 3, further comprising:
    responsive to the score assigned to the anticipated health impact on the user of the identified conditions at the geographic location exceeding the threshold value:
        automatically initiating an order for the at least one medication for the user, the at least one medication for the user selected to alleviate or mitigate the anticipated heath impact on the user of the identified conditions at the geographic location; and
        automatically scheduling the at least one medication to be delivered to the user or available for pickup by the user at the geographic location.

5. The method of claim 3, further comprising:
    responsive to the score assigned to the anticipated health impact on the user of the identified conditions at the geographic location exceeding the threshold value:
        automatically creating a prescription for the at least one medication for the user, the at least one medication for the user selected to alleviate or mitigate the anticipated heath impact on the user of the identified conditions at the geographic location; and
        automatically scheduling the at least one medication to be delivered to the user or available for pickup by the user at the geographic location.

6. The method of claim 1, further comprising:
    responsive to the score assigned to the anticipated health impact on the user of the identified conditions at the geographic location exceeding the threshold value:
        automatically creating an appointment for the user to visit a medical care provider; and
        automatically notifying the medical care provider of the anticipated health impact on the user of the identified conditions at the geographic location.

7. The method of claim 1, further comprising:
    responsive to the score assigned to the anticipated health impact on the user of the identified conditions at the geographic location exceeding the threshold value, automatically suggesting to the user alternative travel plans, the alternative travel plans suggesting replacing plans for the user to travel to the identified geographic location with plans for the user to travel to a new geographic location having conditions less severe than at the identified geographic location.

8. The method of claim 1, further comprising:
    responsive to the score assigned to the anticipated health impact on the user of the identified conditions at the geographic location exceeding the threshold value, automatically scheduling alternative travel plans for the user, the alternative travel plans replacing plans for the user to travel to the identified geographic location with plans for the user to travel to a new geographic location having conditions less severe than at the identified geographic location.

9. A system, comprising:
    a processor programmed to initiate executable operations comprising:
    determining an intent by a user to travel;
    identifying a geographic location to which the user intends to travel;
    identifying medical information pertaining to the user;
    identifying conditions at the geographic location, to which the user intends to travel, that impact health of human beings;
    creating a health impact model for the user, the health impact model comprising a plurality of different types of data, wherein the data is combined into the health impact model using regression analysis or feature clustering, and the health impact model incorporating the identified conditions at the geographic location that impact health of human beings and the identified medical information pertaining to the user, the health impact model analyzing the identified conditions at the geographic location in a context of the identified medical information pertaining to the user, and the health impact model determining an anticipated health impact on the user of the identified conditions at the geographic location based on the identified conditions at the geographic location, the identified medical information pertaining to the user by simulating the health impact of the identified conditions on the user using a cognitive analytics system;

based on the analyzing by the health impact model, assigning a score to the anticipated health impact on the user of the identified conditions at the geographic location;

determining whether the score assigned to the anticipated health impact on the user of the identified conditions at the geographic location exceeds a threshold value; and responsive to the score assigned to the anticipated health impact on the user of the identified conditions at the geographic location exceeding the threshold value, automatically communicating an electronic message to a medical practitioner, the electronic message comprising a hyperlink to a webpage where the medical practitioner provides advisement information, receiving via the webpage the advisement information from the medical practitioner, and communicating to the user an electronic message comprising the advisement information.

10. The system of claim 9, the executable operations further comprising:

determining whether the geographic location is a location where the user has traveled to at least a threshold number of times over a past particular time frame;

wherein the identifying the conditions at the geographic location is responsive to determining that the location is not where the user has traveled to at least the threshold number of times over the past particular time frame.

11. The system of claim 9, the executable operations further comprising:

responsive to the score assigned to the anticipated health impact on the user of the identified conditions at the geographic location exceeding the threshold value, determining an anticipated impact of at least one medication at alleviating or mitigating the anticipated health impact on the user of the identified conditions at the geographic location by performing an analysis of the at least one medication in a context of the identified conditions at the geographic location and the medical information pertaining to the user.

12. The system of claim 11, the executable operations further comprising:

responsive to the score assigned to the anticipated health impact on the user of the identified conditions at the geographic location exceeding the threshold value:

automatically initiating an order for the at least one medication for the user, the at least one medication for the user selected to alleviate or mitigate the anticipated heath impact on the user of the identified conditions at the geographic location; and automatically scheduling the at least one medication to be delivered to the user or available for pickup by the user at the geographic location.

13. The system of claim 11, the executable operations further comprising:

responsive to the score assigned to the anticipated health impact on the user of the identified conditions at the geographic location exceeding the threshold value:

automatically creating a prescription for the at least one medication for the user, the at least one medication for the user selected to alleviate or mitigate the anticipated heath impact on the user of the identified conditions at the geographic location; and automatically scheduling the at least one medication to be delivered to the user or available for pickup by the user at the geographic location.

14. The system of claim 9, the executable operations further comprising:

responsive to the score assigned to the anticipated health impact on the user of the identified conditions at the geographic location exceeding the threshold value:

automatically creating an appointment for the user to visit a medical care provider; and automatically notifying the medical care provider of the anticipated health impact on the user of the identified conditions at the geographic location.

15. The system of claim 9, the executable operations further comprising:

responsive to the score assigned to the anticipated health impact on the user of the identified conditions at the geographic location exceeding the threshold value, automatically suggesting to the user alternative travel plans, the alternative travel plans suggesting replacing plans for the user to travel to the identified geographic location with plans for the user to travel to a new geographic location having conditions less severe than at the identified geographic location.

16. The system of claim 9, the executable operations further comprising:

responsive to the score assigned to the anticipated health impact on the user of the identified conditions at the geographic location exceeding the threshold value, automatically scheduling alternative travel plans for the user, the alternative travel plans replacing plans for the user to travel to the identified geographic location with plans for the user to travel to a new geographic location having conditions less severe than at the identified geographic location.

17. A computer program product, comprising:

a computer readable storage medium having program code stored thereon, the program code executable by a data processing system to initiate operations including:

determining an intent by a user to travel;

identifying a geographic location to which the user intends to travel;

identifying medical information pertaining to the user;

identifying conditions at the geographic location, to which the user intends to travel, that impact health of human beings;

creating a health impact model for the user, the health impact model comprising a plurality of different types of data, wherein the data is combined into the health impact model using regression analysis or feature clustering, and the health impact model incorporating the identified conditions at the geographic location that impact health of human beings and the identified medical information pertaining to the user, the health impact model analyzing the identified conditions at the geographic location in a context of the identified medical information pertaining to the user, and the health impact model determining an anticipated health impact on the user of the identified conditions at the geographic location based on the identified conditions at the geographic location, the identified medical information pertaining to the user by simulating the health impact of the identified conditions on the user using a cognitive analytics system;

based on the analyzing by the health impact model, assigning a score to the anticipated health impact on the user of the identified conditions at the geographic location;

determining whether the score assigned to the anticipated health impact on the user of the identified conditions at the geographic location exceeds a threshold value; and responsive to the score assigned to the anticipated health impact on the user of the identified conditions at the geographic location exceeding the threshold value, automatically communicating an electronic message to a medical practitioner, the electronic message comprising a hyperlink to a webpage where the medical practitioner provides advisement information, receiving via the webpage the advisement information from the medical practitioner, and communicating to the user an electronic message comprising the advisement information.

18. The computer program product of claim 17, wherein the program code is executable by the data processing system to initiate operations further comprising:

determining whether the geographic location is a location where the user has traveled to at least a threshold number of times over a past particular time frame;

wherein the identifying the conditions at the geographic location is responsive to determining that the location is not where the user has traveled to at least the threshold number of times over the past particular time frame.

19. The computer program product of claim 17, wherein the program code is executable by the data processing system to initiate operations further comprising:

responsive to the score assigned to the anticipated health impact on the user of the identified conditions at the geographic location exceeding the threshold value, determining an anticipated impact of at least one medication at alleviating or mitigating the anticipated health impact on the user of the identified conditions at the geographic location by performing an analysis of the at least one medication in a context of the identified conditions at the geographic location and the medical information pertaining to the user.

20. The computer program product of claim 17, wherein the program code is executable by the data processing system to initiate operations further comprising:

responsive to the score assigned to the anticipated health impact on the user of the identified conditions at the geographic location exceeding the threshold value, automatically scheduling alternative travel plans for the user.

\* \* \* \* \*